US009005214B2

(12) United States Patent
Kleiner

(10) Patent No.: US 9,005,214 B2
(45) Date of Patent: *Apr. 14, 2015

(54) METHOD AND SYSTEM FOR IDENTIFICATION OF A CENTER OF A VERTEBRAL DISC SPACE AND CORRESPONDING CENTRAL AXIS OF A SPINAL COLUMN

(71) Applicant: Jeffrey B. Kleiner, Denver, CO (US)

(72) Inventor: Jeffrey B. Kleiner, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/228,593

(22) Filed: Mar. 28, 2014

(65) Prior Publication Data

US 2014/0214102 A1    Jul. 31, 2014

Related U.S. Application Data

(63) Continuation of application No. 13/023,279, filed on Feb. 8, 2011, now Pat. No. 8,690,887.

(60) Provisional application No. 61/302,357, filed on Feb. 8, 2010.

(51) Int. Cl.
| *A61B 17/60* | (2006.01) |
| *A61F 2/00* | (2006.01) |
| *A61B 17/00* | (2006.01) |
| *A61F 2/46* | (2006.01) |
| *A61F 2/44* | (2006.01) |

(52) U.S. Cl.
CPC ............ *A61B 17/00* (2013.01); *A61F 2/442* (2013.01); *A61F 2/4657* (2013.01); *A61F 2002/4658* (2013.01)

(58) Field of Classification Search
USPC ............. 606/86 R, 87, 99, 102, 104; 33/512, 33/520, 644, 670, 672–674, 558.01, 33/558.04, 558.2
See application file for complete search history.

(56) References Cited

U.S. PATENT DOCUMENTS

| 1,221,668 | A | * | 4/1917 | Brunton ..................... 33/808 |
| 2,499,754 | A | * | 3/1950 | Huls ......................... 33/27.01 |
| 3,008,239 | A | * | 11/1961 | Lange ..................... 33/558.04 |
| 3,704,707 | A |   | 12/1972 | Halloran |
| 4,318,226 | A | * | 3/1982 | Engelhart ................... 33/41.5 |
| 4,331,381 | A | * | 5/1982 | Hunter ....................... 359/442 |
| 4,720,921 | A | * | 1/1988 | Beaudry ..................... 33/457 |
| 4,734,992 | A | * | 4/1988 | Scott ......................... 33/403 |
| 5,115,571 | A | * | 5/1992 | Mackin .................. 33/558.04 |
| 6,081,741 | A | * | 6/2000 | Hollis ........................ 600/424 |
| 6,180,085 | B1 |  | 1/2001 | Achilefu et al. |

(Continued)

OTHER PUBLICATIONS

Gilad et al. "Sagittal evaluation of elemental geometrical dimensions of human vertebrae," Journal of Anatomy, Dec. 1985, vol. 143, pp. 115-120.

(Continued)

*Primary Examiner* — Anu Ramana
*Assistant Examiner* — Jessica Weiss
(74) *Attorney, Agent, or Firm* — Sheridan Ross P.C.

(57) ABSTRACT

An apparatus for locating a central axis of a spinal column and method of using the same is disclosed. The apparatus and method includes one or more members capable of spanning a center line which may then be identified by at least one additional member positioned therebetween. Furthermore, the device may contain or be capable of accommodating various additional tools for marking the location of the central axis of a spinal column.

17 Claims, 6 Drawing Sheets

(56) References Cited

U.S. PATENT DOCUMENTS

| | | | |
|---|---|---|---|
| 6,805,669 B2 * | 10/2004 | Swanbom | 600/437 |
| 6,877,242 B2 * | 4/2005 | Mackin et al. | 33/558.01 |
| 6,914,930 B2 | 7/2005 | Raskin et al. | |
| 6,982,740 B2 | 1/2006 | Adair et al. | |
| 7,558,617 B2 | 7/2009 | Vilsmeier | |
| 7,567,834 B2 | 7/2009 | Clayton et al. | |
| 7,577,473 B2 | 8/2009 | Davis et al. | |
| 7,637,917 B2 | 12/2009 | Whitfield et al. | |
| 8,690,887 B2 * | 4/2014 | Kleiner | 606/102 |
| 2002/0156365 A1 * | 10/2002 | Tsekos | 600/411 |
| 2003/0083688 A1 | 5/2003 | Simonson | |
| 2006/0235520 A1 * | 10/2006 | Pannu | 623/17.11 |
| 2007/0005071 A1 * | 1/2007 | Kucklick | 606/76 |
| 2007/0242869 A1 | 10/2007 | Luo et al. | |
| 2008/0215078 A1 * | 9/2008 | Bennett | 606/166 |
| 2008/0306408 A1 * | 12/2008 | Lo | 600/587 |
| 2009/0101158 A1 * | 4/2009 | Kozak et al. | 128/898 |
| 2009/0222011 A1 | 9/2009 | Lehuec et al. | |
| 2009/0259123 A1 | 10/2009 | Navab et al. | |
| 2009/0270873 A1 | 10/2009 | Fabian | |
| 2009/0299477 A1 | 12/2009 | Clayton et al. | |
| 2009/0304143 A1 | 12/2009 | Pakzaban | |
| 2009/0306679 A1 * | 12/2009 | Murphy | 606/130 |
| 2010/0010367 A1 | 1/2010 | Foley et al. | |
| 2010/0010494 A1 | 1/2010 | Quirno | |

OTHER PUBLICATIONS

Official Action for U.S. Appl. No. 13/023,279, mailed Nov. 6, 2012, 9 pages. (Restriction Requirement).
Official Action for U.S. Appl. No. 13/023,279, mailed Dec. 28, 2012, 9 pages.
Final Action for U.S. Appl. No. 13/023,279, mailed Jul. 30, 2013, 16 pages.
Notice of Allowance for U.S. Appl. No. 13/023,279, mailed Nov. 18, 2013, 11 pages.

* cited by examiner

METHOD AND SYSTEM FOR IDENTIFICATION OF A CENTER OF A VERTEBRAL DISC SPACE AND CORRESPONDING CENTRAL AXIS OF A SPINAL COLUMN

This application is a continuation of U.S. patent application Ser. No. 13/023,279, filed on Feb. 8, 2011 (now U.S. Pat. No. 8,690,887), which claims the benefit of U.S. Provisional Patent Application Ser. No. 61/302,357, filed on Feb. 8, 2010, the entire disclose of which is hereby incorporated by reference.

FIELD OF THE INVENTION

The present disclosure relates generally to a method and apparatus for use in spinal surgery. More specifically, the present disclosure relates to instruments for locating and marking points along a spinal vertebra column and/or along the anterior longitudinal ligament. Identification of a center of a vertebral disc and corresponding central axis of a spinal column facilitates various procedures, such as disc arthroplasty.

BACKGROUND OF THE INVENTION

The human spinal column is generally divided into three sections: the cervical, thoracic, and lumbar spine. Portions of the spine, known as vertebrae, are divided by intervertebral discs. Due to a variety of stresses and forces imparted upon the spinal column, damage to intervertebral discs is not uncommon. Conventional methods of treating and repairing damaged discs include spinal arthrodesis (i.e. spinal fusion) and surgical replacement of a disc with an artificial disc (i.e. disc arthroplasty).

When performing these and other procedures, it may be important or necessary to determine a specific location along the spinal column or among the various vertebral bodies, such as the center axis of the spinal column, so that the surgeon may locate and/or mark control parts for completing one of the various procedures conducted with reference thereto. Locating the center axis of a spine, however, may prove difficult given the variations in patient anatomy that may result from, for example, patient size, abnormalities of the spine and surrounding structure, and an absence of typical anatomical landmarks. Other problems that contribute to the difficulty of locating markers in a patient include limited visibility due to the presence of tissue, blood, etc., or the lack of adequate lighting, or the presence of tools or devices placed in the patient to complete the surgery. Locating markers within a patient during minimally invasive surgery may also be difficult due to visual constraints.

Methods for identifying working points about a spinal column utilizing radiographic means are known in the art. For example, U.S. Patent Application Publication No. 2007/0242869 to Luo et al., which is hereby incorporated by reference in its entirety, discloses a method for acquiring radiographic images of a spine and locating and calculating geometrical information, including the center line of the spine. However, images obtained by radiographic means may be of limited value in determining a center axis of the spine, may require additional expenditure of time, expense, and effort to obtain such images, sometimes resulting in misidentification or miscorrelation of anatomical features and radiographic images, etc. Moreover, obstructions resulting from a patient's size and the potential presence/absence of anatomic landmarks that are required to determine the center line by radiographic mapping create practical problems. The invention of Luo et al. and similar methods further subject the patient to radiation exposure which may be undesirable.

Various methods and devices which employ radiographic means suffer from various drawbacks and complications. These include, for example, the need to subject both a patient and a physician or user to radiation, time consuming preparation and administration of radiologic techniques, and the potential for inaccurate or inconclusive results due to the presence of anatomical anomalies or absence of anatomical landmarks.

Therefore, there is a need for an instrument and method capable of accurately and repeatedly identifying one or more points along a spinal column, such as a center axis of a spine. There is further need to economically and quickly, during a surgical procedure, determine these points or "markers" without relying upon radiographic imaging and that otherwise addresses the problems associated with prior art methods. The following disclosure describes an instrument that employs a novel combination of features that address these long felt needs and further describes a method for using the same.

SUMMARY OF THE INVENTION

The present invention improves upon various known devices by providing an instrument that takes advantage of various features of the human spine to identify, target, and/or mark the location of a center axis of a spine. According to one embodiment, this instrument may further be used in minimally invasive procedures.

Various embodiments of the present invention, as described herein, rely upon certain anatomical consistencies in order to isolate, identify, target, and/or mark certain features or locations. For example, devices of the present invention may be used in conjunction with a human Anterior Longitudinal Ligament ("ALL"). The ALL is known to generally traverse a longitudinal distance of a spine, with the center of the ALL in lateral alignment with a central axis of the spinal column. Devices and features of the present invention may be used to identify and/or measure a center position of an ALL and thereby determine the central axis of a patient's spine. The present invention further contemplates use in identification of various other ligaments and regions of the human body to assist in various procedures.

U.S. Patent Application Publication No. 2009/0222011 to Lehuec et al., which is hereby incorporated by reference in its entirety, discloses a targeting instrument for use in spinal disc replacement operations. Lehuec et al. discloses a device to be inserted between vertebral members of a patient and aligned with a mid-line of the spine. However, Lehuec et al. does not teach a method or apparatus capable of locating the mid-line without the use of radiographic imagining. Lehuec et al. further discloses a device that is not suited for minimally invasive procedures and which is more suited for procedures that are relatively time consuming.

U.S. Patent Application Publication No. 2009/0270873 to Fabian, which is hereby incorporated by reference in its entirety, discloses a surgical inserter for inserting an implant into a vertebral space. Portions of such devices may be used in addition to in place of various components of the present invention. For example, in one embodiment, a grip and grip activator may be used to measure and/or make contact with the peripheral boundaries of an ALL.

U.S. Patent Application Publication No. 2009/0299477 to Clayton et al. discloses a method and system for implantation of a device between two vertebral bodies using image guided surgical navigation, and is hereby incorporated by reference in its entirety. Clayton et al., however, fails to teach a device and method that does not require image sensing devices to locate a central axis of the spine. Clayton et al. discloses a device which contemplates the use of an image sensing device apart from human observation and a corresponding imaging display mechanism. Accordingly, Clayton et al. fails to teach several novel aspects of the present invention.

U.S. Patent Application Publication No. 2009/0304143 to Pakzaban, which is hereby incorporated by reference in its entirety, discloses a device and method for non-invasively locating a spinal segment using laser diodes and a method of marking a patient's skin with an estimated location of a central axis with additional information provided by an X-ray source. Pakzaban discloses a device and method which requires the use of radiologic imaging and that further does not provide for the ability to mark portions of a spine and/or surrounding tissue with an indication of a central axis.

According to varying embodiments disclosed herein, the present invention may be comprised of a central body portion, hinged members, marking devices, apertures to accommodate marking devices, adjustable fasteners, clamps, screws, etc., and members extending to various peripheral locations of an ALL. Embodiments of the present invention may be used, for example, in identifying a central axis of a spine with reference to the ALL. In one embodiment, the present invention comprises extending members for contacting both lateral peripheral boundaries of an ALL. Contact between extending members with both lateral peripheral boundaries of an ALL simultaneously positions at least a third member/portion of the invention with a center line/point of the ALL, which corresponds with a center line/point of a spinal column.

In one embodiment, the present invention utilizes hinged or pivoting and/or extending members capable of accommodating various ALLs. For example, two or more hinged members may be employed to determine the lateral peripheries of an ALL and thereby determine a center line of the ALL and spinal column based on the communication between the hinged members and a common axis of rotation. In another embodiment, the present invention may further include one or more additional means for marking or otherwise identifying the location of a central spinal axis. For example, a common axis of rotation of two hinged members may further include an aperture or means for accommodating a chisel or electrode device and thereby allow for the marking of the lateral positioning of a center axis of a spine. Thus, in one embodiment, the present invention comprises a device for identification of a center of a vertebral disc and corresponding central axis of a spinal column, further comprising:

a first and second member of substantially similar length/dimensions having first and second ends and hinged about a common axis;

the first and second members further comprising extending members with extend substantially perpendicularly to the first and second member;

a third member having a first end and a second end and hinged about an axis generally perpendicular to the common axis; and the second end of the third member representing a point equidistant from the second ends of the first and second members.

In an alternative embodiment, the present invention comprises a device for identification of a center of a vertebral disc and corresponding central axis of a spinal column, further comprising:

a first and second member of substantially similar length/dimensions having first and second ends and hinged about a common axis;

the first and second members extending from a main portion;

the center of the main portion being equidistant from the second ends of the first and second members; and wherein the main portion further comprises an aperture useful for indicating, visualizing, and/or marking a point equidistant from the second ends of the first and second member.

In various embodiments, aspects of the present invention comprise a handheld portion to facilitate user manipulation and use of the device. A single handheld portion, suited to fit in a surgeon's hand(s), is provided that is in communication with various patient contacting portions of the present invention. For example, at least two extending members may be in communication with a handheld/handle portion that are capable of contracting or translating to identify the peripheral boundaries of an ALL or similar anatomical feature. A trigger mechanism can be employed to permit the surgeon to depress a trigger and thus cause patient contacting elements to move in a predetermined fashion about a patient's ALL boundaries. A third member, such as a marking device, a laser, an additional extending member, or other similar zone and/or point identifying device may additionally extend or emanate from the handheld portion. Such embodiments allow a user to place a device in a desired position with relative ease and reduced risk of slippage or dropping of the device.

In another embodiment, once a user properly positions the device, features and methods of the present invention may be activated. For example, a dial, button, or similar actuating device may be provided on a handheld portion which allows a user to activate the contraction of extending members or positional devices. Extending members may additionally comprise contact sensing elements that terminate the contraction of extending members and/or provide feedback to a user that contact with an object (e.g. an ALL) has been made. Embodiments of the present invention may further include means for identifying and/or marking a center line once this contraction or similar motion is completed. For example, once an object is identified by the previously described contraction, a user may activate a component within or in addition to the handheld portion to generate a mark or indication of the location of a particular location, preferably a center line and/or point. In one embodiment, a button may be pressed to project a laser or light upon a center line. Alternatively, a marking device such as a Bovie® pen may be deployed from the handheld portion to mark a center line. In alternative embodiments, handheld portions may include ports, apertures, slots, recesses, or similar features to accommodate additional devices to be inserted through the handheld portion. Various devices and methods of the present invention may therefore be operated or performed without the need to use two hands.

Embodiments comprising a handheld device may further comprise various elements/features at the working end of the device that are useful for determining a centerline. For example, an arced measurement device (e.g. protractor) may be disposed proximal to a handheld portion of the device that is further capable of being positioned (e.g. proximal or adjacent to) with respect to an ALL or similar object. In various embodiments, the arced measurement device may be transparent or translucent to allow for complete viewing of an ALL or similar object and its boundaries. Accordingly, symmetrical features of an arced measurement device may be aligned with lateral boundaries of an object such as an ALL, thus allowing for a corresponding point equidistant from the symmetrical features to represent the centerline of an object. Such a device may further include marking devices that correspond with the point equidistant from the symmetrical features, and thus, certain embodiments include at least two apertures through which a surgeon can extend a pin or other marking device therethrough to identify a particular point, e.g. a center-point or line. For example, a handheld portion of the device may comprise a trigger or actuator to deploy or actuate devices/elements that may at least temporarily mark the measured equidistant point.

Accordingly, in one embodiment, the present invention comprises an arcuate transparent device capable of measuring at least two points of an object and indicating at least a third point that is equidistant from the at least two points of an object and that further comprises a handle or gripping portion. The device and method of use may further include means for visualizing and/or marking the third point.

Attachments to the handle may be reversibly associated therewith, thus permitting disposable elements (e.g. the protractor unit, the dual-pronged movable arms, etc.) to be associated for particular surgeries or procedures. For example, for small individuals, infants, etc. a one-sized handle grip for a surgeon can accommodate different sized and/or configured working attachments.

In yet another embodiment, the present invention contemplates various deployable features which may be useful in identifying a center line, center plane, or center position between two points. For example, once various features of the present invention are appropriately positioned on either side of an object, a device which is located equidistant to these features may be depressed, ejected, or dispelled from the present invention. For example, a tack or marker capable of attaching or adhering to an object may reside at the center point of the present invention. Such a device, when properly positioned by additional components of the present invention, may be deployed so that it remains (e.g. for a time during surgical procedures and/or permanently) to indicate a center line/plane, and the remainder of the device removed from the work area. Deployable devices of the present invention may comprise phosphorescent or luminescent materials. Embodiments of the present invention have uses in three-dimensional surgical procedures, as it is important therein to define a center point or plane for various purposes.

In yet another embodiment, devices of the present invention may measure a width of an object and determine and/or identify the presence of a centerline without requiring physical contact between the device and the object. For example, a device may be provided that allows a user to direct or guide two points of light (e.g. lasers) to desired positions (e.g. the lateral boundaries of an ALL or similar object). Once this is accomplished, the device can calculate the distance between these points and further produce, provide, emanate, etc. an additional mark or reference point indicating the position of a centerline. Embodiments of the present invention measure and/or identify a centerline through purely physical features and, in certain embodiments, incorporate logic to determine a centerline point and/or means for positioning a marker at the centerline point.

Accordingly, devices of the present invention include a handheld portion in communication with extending members that do one of, and preferably at least two of the following: measuring, identifying, and/or marking various features of an anatomical object, while leaving said devices free for manipulation by one hand of a user. Various features of U.S. Pat. No. 7,577,473 to Davis et al. and U.S. Pat. No. 7,637,917 to Whitfield et al., which are hereby incorporated by reference in their entireties, may be incorporated into handheld features of the present invention. Those of skill in the art will recognize that various ALL measuring devices may be interchangeable between various handheld portions of the present invention as described herein.

In various embodiments, apertures, slots, and/or means for accommodating a chisel or electrode device may include portions of the device which can accommodate, guide, or direct a device that is useful for marking a point indicated by the device. Where various features described herein are referred to as slots, tubes, or apertures, one of skill in the art will understand that various other means that are capable of receiving additional devices are within the scope and spirit of the present invention. For example, a central point of the present invention may be located at the center of an annular portion which is sized to accommodate known commercial devices, such as a Bovie® pen or various known chisels. Accordingly, known devices may be received by the annular portion in a manner that ensures marking at a central location of the device. Aspects of the present invention may further include, or provide for the reception of, marking devices which utilize radiographic ink, luminescent ink, bone scarring devices, and various other marking methods. For example, various inks suitable for use within a surgical cavity, including luminescent inks, may be applied to a portion of a spine or ALL. The application of these inks may be accomplished, at least in part by, features of the present invention. Dyes such as those disclosed in U.S. Pat. No. 6,180,085 to Achilefu et al., which is hereby incorporated by reference in its entirety, may be employed. Inks and dyes suitable for use within a surgical workspace may consist of those visible to the naked eye as well as various dye and inks which require additional imaging or viewing means. Various embodiments may also include marking and other devices as described herein as a portion of the main body of the device (i.e. integrated within a portion of the device).

Various features of the present invention may be comprised of translucent or transparent materials which may reduce the amount of visual obstruction posed by a device. For example, one or more portions of a device may be comprised of a plastic, Lucite, or other similar translucent material which allows a user to visualize portions of a spine or similar feature that may be obstructed by opaque materials. Furthermore, devices and components may be disposed within transparent or translucent materials to further aid in visualization and targeting of certain objects. In one embodiment, cross-hairs or similar targeting features may be employed within or proximal to features of the present invention. Where translucent features are incorporated into the invention, these targeting features may be disposed within translucent features and help identify, guide, or target various other devices and procedures.

Materials and devices may also be employed that act to aid in visualization. Magnifying lenses may be incorporated into various features of the present invention. For example, various known lenses may be placed over an aperture or slotted portion in order to magnify and provide greater visualization of a workspace, including, by way of example and not limitation, a center point of an ALL.

Various projection means may be incorporated into embodiments of the present invention. For example, known methods of projecting lasers and/or similar markers, such as those described in U.S. Pat. No. 6,914,930 to Raskin et al. for a laser level, may be used to project a point or line along an axis that has been identified as described herein.

Various features of the present invention may also be illuminated. Illumination means, such as LED lights and similar devices may be employed in various different positions on disclosed embodiments. For example, an LED may be positioned at a central point of the present invention in order to cast light into a surgical work area. Lighting means may also be employed at the distal ends of various members to assist in visualization of the members and member extremities when working within a dark, crowded, and/or obstructed area. Lighting means may include, for example, various "glow in the dark" or phosphorescent materials. Various features of the present invention may be composed of or coated with known phosphorescent materials.

Apertures, slots, compartments, and/or means for accepting a marking device may further be capable of accommodating various cannulas for minimally invasive surgical procedures. Cannula devices suitable for spinal surgery, such as those disclosed in U.S. Patent Application Publication No. 2003/0083688 to Simonson and various other devices known in the art may be employed within various features of the present invention. In one embodiment, apertures, slots, passages, etc. adapted to receive a cannula have at least edge regions comprising a material distinct from the remainder of the device, including transparent aspects and/or flexible or malleable regions that facilitate ease of positioning by a surgeon.

Embodiments of the present invention may further include the ability to adjust the length of one more members. Providing for adjustability of various members may allow for a single device to accommodate a wide array of patients who may vary in size and various corresponding dimensions (e.g. depth to a spinal column, lengths of various portions of the spinal column, etc.). As described herein, adjustability about two or three distinct axis is preferred to permit surgeons to make minimal adjustments to accommodate surgical situations that arise. Thus, nested or telescoping members, preferably having at least one flexible component, provide a surgeon with the ability to address the desired positional orientation of instruments as they relate to a patient's physical features.

In various embodiments, aspects of the present invention may comprise disposable devices. In one embodiment, the entirety of a device may be formed from one or more relatively inexpensive materials which enable devices to be discarded and replaced after each use, thus avoiding autoclaving and other sterilization procedures. In an alternative embodiment, specific portions of the present invention may be detachable from a remainder of the device and discarded after use. By way of example only, extending members as will be described may be removable from a main portion of the device, disposable, and/or comprised of a material that provides for relative ease of replacement. Devices of the present invention may be comprised, at least in part, of polyether ether ketone (or PEEK).

In alternative embodiments, the present invention incorporates reusable components, such as surgical grade metals and plastics which may be autoclaved or similarly cleaned and sanitized for reuse in subsequent procedures.

The present invention may additionally interface with various external display units and/or devices. U.S. Pat. No. 7,558,617 to Vilsmeier, which is hereby incorporated by reference in its entirety, discloses a neuro-navigation system comprising reflector referencing devices and a marker system for mapping various aspects of a patient. The present invention may, for example, interface with various different devices such as a surgical microscope, an ultrasonic diagnostic system, computer aided remote surgical operation systems, and/or various other devices. In yet another embodiment, the present invention includes a method which further contemplates the use of various nerve testing devices, such as those disclosed in U.S. Patent Application Publication No. 2010/0010367 to Foley et al. which is hereby incorporated by reference in its entirety.

In various embodiments, the present invention is employed in conjunction with various known imagining devices and serves as a supplemental or verification technique for determining the physical positions of various anatomical structures. For example, when various known radiological devices are used to map or determine the locations of various features or anatomical structures, embodiments of the present invention further operate to confirm, evaluate, verify, etc. the information obtained from such radiological devices. Similarly, embodiments of the present invention are alternatively used to acquire preliminary data on the location of anatomical features which are later confirmed or evaluated by radiological and other similar imaging devices and procedures. Various visualization methods and devices which may be used in conjunction with the present invention include, for example, those described in U.S. Patent Application Publication No. 2009/0259123 to Navab et al., which is hereby incorporated by reference in its entirety.

In yet another embodiment of the present invention, various devices, such as touch-sensors or proximity sensors, may be provided in order to detect when certain portions of the present invention are proximate to or have made contact with, for example, an ALL. The device may further provide feedback to a user based on the information received from such devices. For example, an LED light may indicate that contact with an ALL has been made and that no further contraction of the present invention is required.

In yet another embodiment, the present invention further incorporates various means for measuring additional dimensions of a disc space. For example, devices similar to those disclosed in U.S. Patent Application Publication No. 2010/0010494 to Quirno, which describes a method and device for determining an optimal size of an intervertebral implant to be inserted within an intervertebral space and is hereby incorporated by reference in its entirety, may be incorporated into embodiments of the present invention.

Methods of determining the location of a disc space center axis, including methods further requiring preparation (e.g. cleaning, marking, etc.) of an ALL and similar anatomical structures are further contemplated by the present invention. For example, as one object of the present invention is to utilize an ALL as an anatomical landmark, a method includes an ALL (or similar object) first being prepared or treated before employing additional features of the present invention. An ALL or similar object may be cleaned and/or marked with various inks, dyes, or fixed objects such as staples, sutures, or other devices which facilitate the visualization of the lateral boundaries of an ALL or similar object. Additionally, conductive elements may be placed on, within, or proximal to an ALL in order to assist in proximity sensing operations. For example, conductive materials, such as metallic elements may be placed at a boundary of an object such that additional contact sensing means disposed on other components of the present invention detect lateral boundaries. One embodiment, for instance includes the following elements:

a) creating an access opening in a patient adjacent the patient's spine;

b) providing a center-locating tool adapted to fit within the access opening, said tool comprising:

i) a handle portion; and ii) a center-line indicating portion operatively associated with said handle portion, said center-line indicating portion having a first component for identifying one border of the patient's ALL and a second component for identifying a separate border of the patient's anterior longitudinal ligament, and a third component for marking a point equidistant from each of said borders;

c) inserting said center-locating tool into the access opening;

d) aligning said first component of said center-line portion with one border of a patient's ALL;

e) aligning said second component of said center-line portion with a separate border of a patient's ALL;

f) marking a point equidistant between said borders using said third component; and g) removing the center-locating tool from said access opening after said marking step.

Although the description of various embodiments herein relates to the use of a device within a surgical workspace, it will be recognized that embodiments of the present may be utilized wherein at least portions of the device are external to a patient's body or a surgical work area. The invention may be utilized completely external to a patient's body, partially external to a patient's body, generally disposed within a surgical area, or completely disposed within a work area. Where devices are to be used at least partially external a patient's body, additional marking devices may be utilized. U.S. Pat. No. 6,805,669 to Swanbom, discloses a method and device for marking skin during an ultrasound examination and is hereby incorporated by reference in its entirety. These and similar techniques and/or devices may be utilized when it is desirable to mark an area external to a surgical cavity. Various imaging devices, such as U.S. Pat. No. 6,982,740 to Adair et al., which is hereby incorporated by reference in its entirety, may be utilized with the present invention, such as to provide illumination sources for handheld embodiments.

These and other advantages will be apparent from the disclosure of the invention(s) contained herein. The above-described embodiments, objectives, and configurations are neither complete nor exhaustive. As will be appreciated, other embodiments of the invention are possible using, alone or in combination, one or more of the features set forth above or described in detail below. Further, this Summary is neither intended nor should it be construed as being representative of the full extent and scope of the present invention. The present invention is set forth in various levels of detail in this Summary, as well as in the attached drawings and the detailed description below, and no limitation as to the scope of the present invention is intended to either the inclusion or non-inclusion of elements, components, etc. in this Summary. Additional aspects of the present invention will become more readily apparent from the detailed description, particularly when taken together with the drawings, and the exemplary claim provided herein.

The drawings are not necessarily to scale.

DETAILED DESCRIPTION OF THE FIGURES

Figure 1:
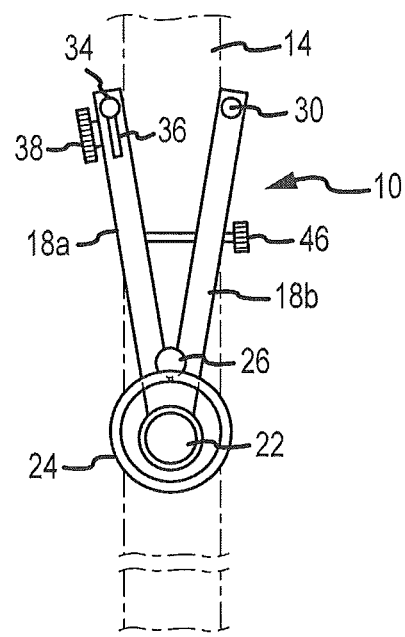
FIG. 1 is top plan view of an instrument for locating one or more points about a spinal column according to one embodiment.
Figure 2:
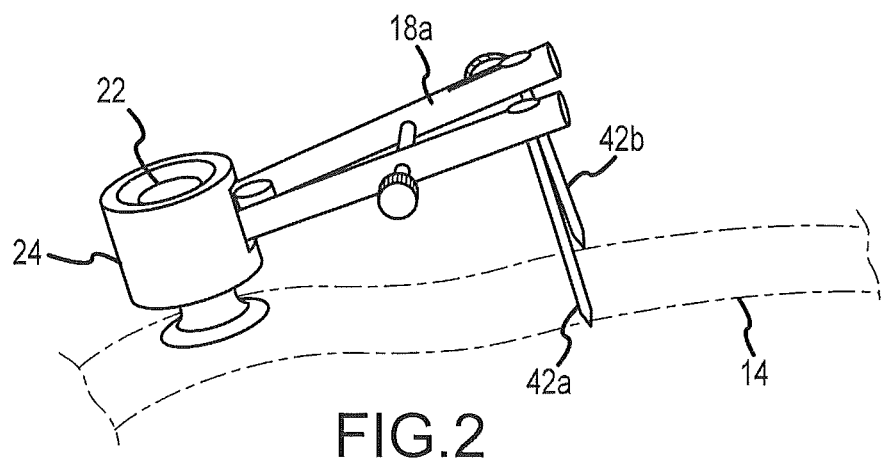
FIG. 2 is a side perspective view of the instrument of FIG. 1.

Referring now to FIGS. 1 and 2, a disc space centering tool according to one embodiment of the present invention is shown. The tool 10 is shown with reference to an ALL 14. The ALL 14 is known to generally span the longitudinal length of an anterior portion of the human spine and align with a central axis of rotation of the spine. Accordingly, the ALL 14 generally provides a useful reference point for measuring, tracking, or otherwise identifying a central axis of a spine for surgical procedures.

In one embodiment, the device 10 includes two or more hinged or movable members 18a, 18b useful for identifying the lateral boundaries of an ALL 14. Hinged members of the present invention may further include perpendicularly extending members 42a, 42b that facilitate in the determination of a width of an ALL 14. For example, perpendicularly extending members 42a, 42b may be comprised of pins or similar extensions that provide for a contact point(s) with the device 10 and an ALL 14.

As one of ordinary skill in the art will recognize, visibility within a surgical workspace may often be obstructed by various tissues and fluids. Accordingly, a clear view of an ALL 14 may not be available. In order to account for this, members 42a, 42b of the present invention provide a means whereby the boundaries of an ALL 14 may be determined through tactile as well as visual feedback, and further via electronic sensing means, such as those employing proximity sensors or computer aided systems (not shown).

In one embodiment, portions of extending members 42a, 42b comprise additional means for sensing the proximity of an ALL 14. For example, various known tactile pressure sensors may be implemented in extending members 42a, 42b that provide indication of contact between an extending member 42 and an ALL 14. Accordingly, a signal corresponding to this contact may be displayed to a user, either on a portion of the device 10 or as part of an external display unit.

Extending members 42a, 42b may be of unitary construction with hinged members 18a, 18b or may be non-fixedly attached to hinged members 18a, 18b and selectively adjustable in various degrees of freedom. For example, extending members 42a, 42b may be constructed or positioned through hinged members 18a, 18b and may further comprise a round or flat head rivet 30, 34 or similar means to prevent undesired movement. Additionally, the device 10 may further comprise means for fixing one or more extending members 42a, 42b in a variety of positions. For example, means for fixing an extending member 42a, 42b may comprise a set screw 38 and a slot 36 which allow for positioning of an extending member 42a, 42b in one or more axis. For example, a slot 36 may provide for the ability to position an extending member 42a, 42b in a non-discrete number of longitudinal and vertical positions. A set screw 38 may further be provided to affix an extending member 42a, 42b in a desired location.

In one embodiment, extending members 42a, 42b may be spring loaded retracting members, capable of retracting within themselves and/or through various portions of the device (e.g. hinged members 18a, 18b). Extending members 42a, 42b may also be coated or comprised of various phosphorescent materials and/or filled with various materials. For example, one embodiment contemplates filling extending members 42a, 42b with ink or dye which may be selectively deployed to mark locations. In an alternative embodiment, extending members 42a, 42b are filled with a phosphorescent material to further aid in visualization and location of various objects, such as an ALL 14.

It will be recognized that certain embodiments of the present invention 10 may require distal points of extending members 42a, 42b to reside in a generally co-planar manner in order to dictate that a central member 24 further resides on a center line of an ALL 14 or similar object. Accordingly, it may be undesirable to adjust a single extending member 42a, 42b without similarly adjusting the second or additional extending member(s). Therefore, in one embodiment of the present invention, extending members 42a, 42b may be in fixed communication with each other such that the distal adjustment of one is physically dependent upon the same magnitude of adjustment of the other. For example, extending members 42a, 42b may be joined or fused together with an additional member which prevents the vertical displacement of one member without the other.

Two or more hinged members 18a, 18b may be joined to a central member 24 such that hinged members share a common axis of rotation. Accordingly, when one or more of the hinged members 18a, 18b is rotated about its hinge, the longitudinal axes of the hinged members 18a, 18b and a line bisecting two hinged members 18a, 18b will intersect at a common point within a central member 24. Accordingly, by placing extending members 42a, 42b of the present invention 10 at the lateral boundaries of an ALL 14, the center line of an ALL 14 may be identified by the resulting position of the attached central member 24. Those of skill in the art will further recognize that the center line of an ALL 14 will correspond to the disc space center line of a patient within a reasonable degree of certainty in most applications.

In one embodiment, a central member 24 of the present invention 10 further comprises means for marking or targeting a center line position. For example, central member 24 may comprise an aperture, tubular member, or other similar member 22 capable of receiving an additional device, which provides for direct visualization and/or access to a spinal/ALL center line. Aperture 22 may accommodate various additional devices, such as surgical tools useful for marking a center line or devices for conducting various surgical procedures within a central member 24. One of skill in the art will recognize various devices useful for marking a position or center line as indicated by the present invention. For example, various chisels and electrodes may be employed to create a physical mark on a portion of a patient's ALL 14 or vertebral disc at a location identified by the present invention as described herein. Alternatively, a laser or light may be positioned to correspond with a center line position as identified by the present invention. Such a device may provide, for example, a non-injurious indication of a disc space axis while disposed within a surgical work space or after the present invention has been removed from a work space.

Alternatively, a central member 24 may comprise a tubular member 22 or other sufficiently large aperture within which various procedures may be conducted. For example, once a center line has been identified according to various embodiments of the present invention, the tubular member or aperture 22 of the device 10 may provide a sufficient workspace within which surgical tools and devices may be accommodated and a user may perform various tasks.

In one embodiment, a disc space centering tool 10 comprises a screw 46 in communication with the plurality of hinged members 18a, 18b for setting and/or maintaining a precise relative position of hinged members 18a, 18b. Such a screw 46 comprises a thumbscrew threaded through one hinged member 18b and at least partially threaded through another hinged member 18a. By adjusting the position of the screw 46, a desired angular displacement between hinged members 18a, 18b may be established and maintained.

A method of use for the previously described device is contemplated whereby hinged members 18a, 18b and a central member 24 may be used to locate and/or identify a central axis of a spinal column. According to one embodiment, hinged members 18a, 18b may be expanded to a desired width and generally situated so that hinged members 18a, 18b are positioned on either lateral boundary of an ALL 14. Once hinged members 18a, 18b are generally situated on either side of an ALL, hinged members 18a, 18b may be contracted to a position where both hinged members 18a, 18b contact the lateral boundaries of the ALL 14. In one embodiment, a user may determine the existence of contact between aspects of the present invention and an ALL 14 through visual observation and/or tactile sensation. In another embodiment, the presence of this contact may be communicated to a user by various sensing means. For example, touch-sensors or similar devices may be implemented into a distal portion of hinged members 18a, 18b that are capable of determining contact between the present invention 10 and an ALL 14. In one embodiment, upon contact with an ALL, touch-sensors of the present invention provide feedback to a user, such as through visual light indicators or audio indicators, that contact has been made and no further contraction of hinged members 18a, 18b is required.

Once the hinged members 18a, 18b have been brought into contact with an ALL 14 or other object whose center line is to be determined, central member 24 may then be used for identifying, targeting, and/or marking a center line of the object identified by hinged members 18a, 18b as previously described. Marking of this center point may be accomplished, by example, through a variety of tools, methods and devices, including, but not limited to, Bovie® pens, chisels, tamping devices, and/or various inks or dyes.

Once a center line has been identified as previously described, it may be marked by various different methods and devices. In one embodiment, central member 24 further comprises means for marking an ALL 14 or object whose center line is to be located. For example, a central member 24 comprises an electrode containing device capable of marking a point representative of a spinal center line. Accordingly, once the device 10 is properly positioned, a user may activate features of such a device to cauterize or mark a point which is to serve as a visual indicator of a center line for the remainder of surgical procedures to be performed. In one embodiment, central member 24 may include an aperture or tubular member 22 through its center capable of accommodating various devices useful for marking a point, such as a Bovie® pen or similar electrode containing device, chisel, or other marking device. In this embodiment, a center line may be marked or indicated by inserting the appropriate device within aperture 22 and performing the appropriate function (e.g. activating the electrode pen or tamping down a chisel to provide a mark).

According to various embodiments, once a center line has been determined and the appropriate mark or indication made, the device 10 may be removed from the work area. It will be recognized, however, that the device 10 may be left within a surgical workspace and continue to serve as a reference point for a center line. For example, where procedures are to be conducted which do not require the level of access and freedom of movement provided by the removal of the device 10, the device 10 may remain within the workspace as a physical indicator of a center line.

It will be recognized that the present invention 10 may be used to identify additional reference points (i.e. those other than a point corresponding to a spinal central axis). For example, once the center of an ALL is determined, the device 10 may be translated to another position without adjusting the angular position of hinged members 18a,b. By doing so, additional points may be identified or marked. These points may, for example, constitute points of equal distance away from a central axis and provide additional reference points in the event that one or more points becomes obstructed from view or simply where it is advantageous to have a plurality of reference points with which to align various objects.

Various embodiments of the present invention further comprise the ability to enable or assist in minimally invasive surgical procedures. For example, a central member 22 of the present invention may be constructed in a manner that allows the device 10 to receive various cannulas and/or minimally invasive surgical devices known to those of skill in the art. In alternative embodiments, aspects of the present invention may be combined or affixed to currently known minimally invasive devices, such as those disclosed in Applicant's U.S. Provisional Patent Application 61/120,260, which is hereby incorporated by reference in its entirety.

Figure 3:
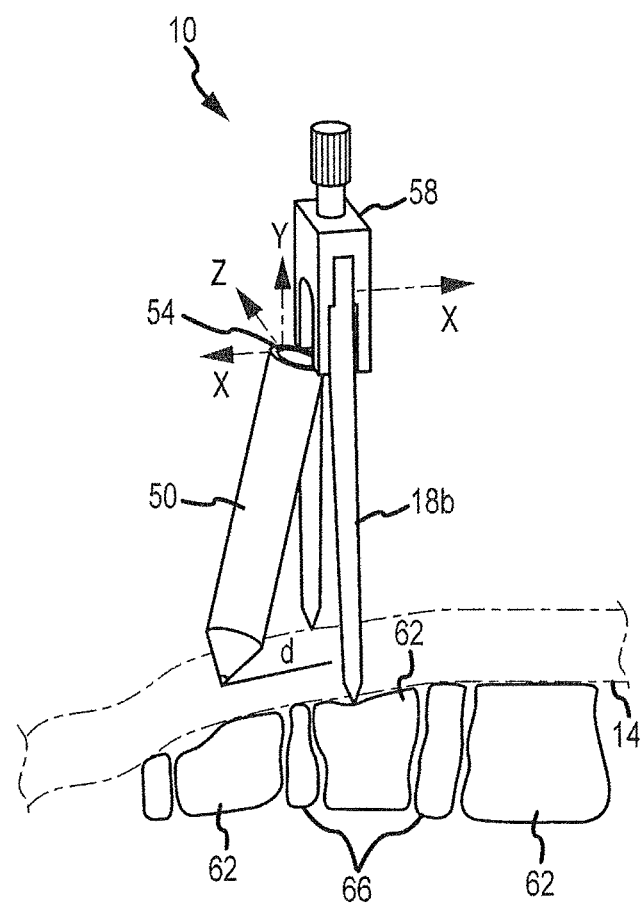
FIG. 3 is a side perspective view of device for identification of a center of a spinal column according to one embodiment.

FIG. 3 is a side perspective view of a disc space centering tool according to one embodiment of the present invention. As shown, hinged members 18a, 18b share a common axis of rotation and are hinged so that members 18a, 18b are always an equal angular displacement away from a center-line bisecting the two members 18a, 18b. Accordingly, hinged members 18a, 18b span and identify the width of a given space, such as an ALL 14, and identify a centerline of the space that is disposed midway between the hinged members 18a, 18b. The device may further include an additional member 50 for identifying a spinal center line. In one embodiment, indicating member 50 is free to rotate about a single axis, where that axis may be perpendicular to the axis of rotation of the other hinged members 18a, 18b. Indicating member 50 may therefore be a pivotable extension of the bisecting line between hinged members 18a, 18b and thus useful for marking or otherwise indicating the midline of an ALL and corresponding spinal midline. In alternative embodiments, one or more of the extending members 50, 18a, 18b are fixedly attached to a connecting portion 58.

It will be recognized that in various spinal procedures, the height of vertebrae 62 and vertebral discs 66, and the different longitudinal distances d that embodiments of the present invention will need to span will be based on patient size and the portion of the spine upon which procedures are to be performed. Accordingly, indicating member 50 may be hingedly attached to a connecting portion 58 by a joint 54 which allows for different distances d to be established. It will also be recognized that similar adjustability may be achieved by providing for extendable or telescoping members 18a,b as shown and described with respect to FIG. 1.

In one embodiment, the device 10 may further include a thumbscrew (46 in FIG. 1) or similar adjustable member useful for adjusting and or securing the rotational position of hinged members 18a, 18b. In another embodiment, a plurality of indicating members 50 are provided. In yet another embodiment, indicating member 50 may comprise telescopic capabilities such that indicating member 50 is free to expand or contract along its own axis and provide additional functionality for marking a point at a distance d away from hinged members 18a, 18b.

Various hinged members of the present invention may be biased or incorporate springs. As used herein, biased may refers to both a linear and non-linear bias or spring force. For example, hinged members 18a, 18b may include one or more springs (e.g. a coil spring extending into both members 18a, 18b) which may bias the movement of the members. In one embodiment, a biasing force may be sufficient to retract hinged members 18a, 18b toward each other at least to an extent that they do not compress an object disposed within the members (e.g. an ALL 14).

Various lighting means and/or mechanisms are further contemplated by the present invention. LED lighting may be provided, for example, at an intersection of members or provided as an extension or attachment to the present invention. It will be recognized that various lighting devices may serve to illuminate a surgical space, particularly where the surgical space is small, dark, and/or obstructed. Lighting means, such as LED lights or fiber-optic lighting may be employed at a distal end of one or more hinged members or at various other points on a device. Such devices are employed to generally illuminate an area and/or to provide a user with additional clarity and visibility as to the distal portions of various features of the present invention.

It is further contemplated that various portions of the present invention may be comprised of generally disposable materials. The entirety or portions of embodiments of the present invention may be comprised of materials generally known to be relatively inexpensive and capable of being discarded after even a single use. For example, members 18a,b, 50 may be comprised of a detachable portion that is discarded after use and replaced with another item of the same or similar construction.

Figure 4A:
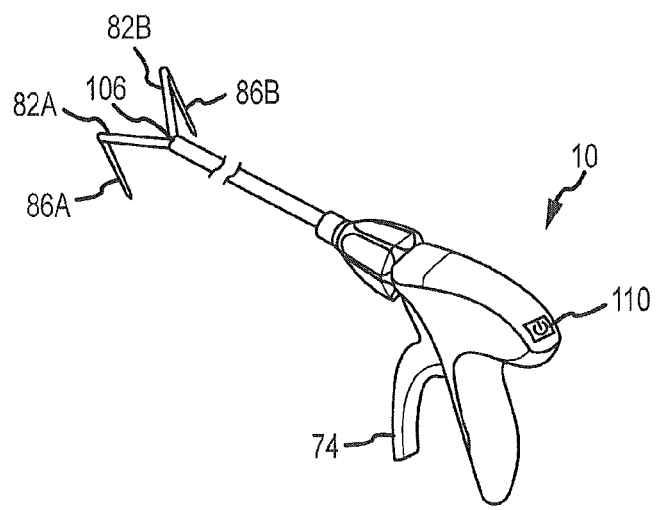
FIG. 4A is a perspective view of a device for identification of a center of a spinal column according to one embodiment.
Figure 4B:
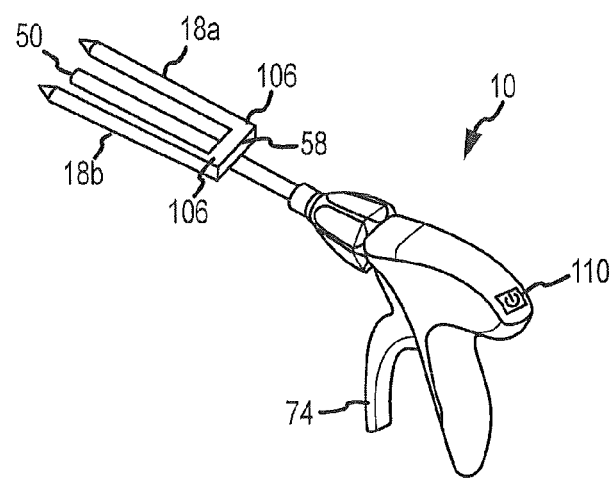
FIG. 4B is a perspective view of a device for identification of a center of a spinal column according to one embodiment.

As shown in FIGS. 4A-4B, various embodiments of the present invention may be disposed upon devices suitable for use with only hand of the user. In one embodiment, hinged members 18a, 18b, 82A, 82B and one or more hinges 106 are provided. Hinged members may be operated via switch 110 which is capable of contracting and/or expanding hinged member 18a, 18b, 82A, 82B. Marking member 50 is further provided to indicate a centerline as measured by hinged members 18a, 18b. Features of marking member 50 may be selectively controlled by a trigger or activation device 74. In various embodiments, these features comprise light or laser emitters, Bovie® pens, and various other similar marking devices.

Figure 6:
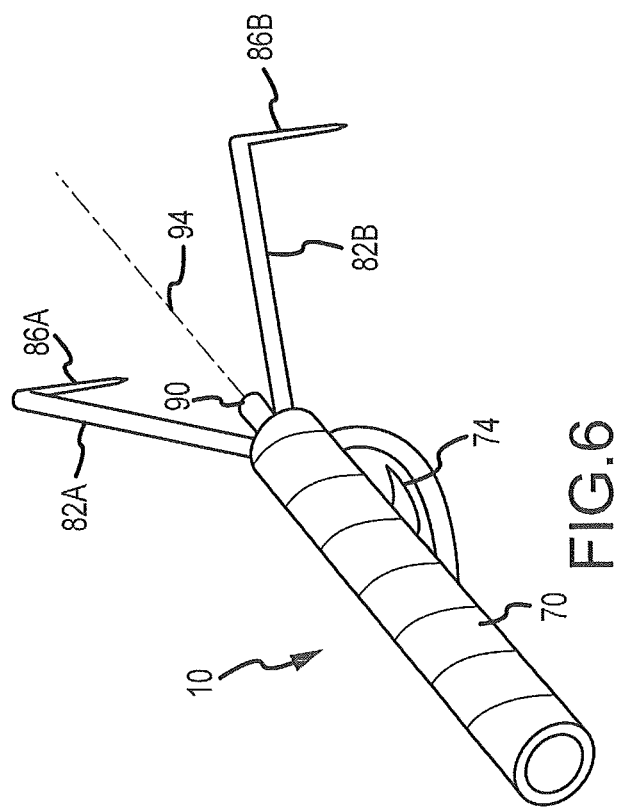
FIG. 6 is a perspective view of yet another device for identification of a center of a spinal column according to one embodiment.
Figure 5:
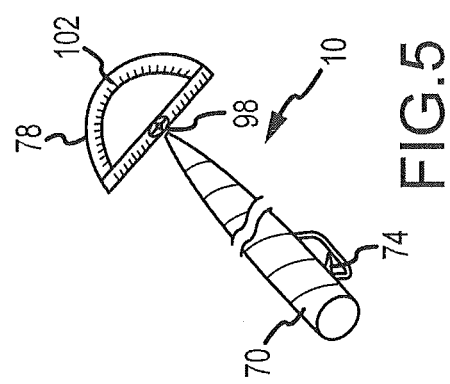
FIG. 5 is a perspective view of yet another device for identification of a center of a spinal column according to one embodiment.

FIGS. 5-6 depict alternative embodiments of the present invention. FIG. 5 depicts an embodiment wherein a measuring device 78 is disposed on the distal end of a handheld portion 70. In one embodiment, the measuring device 78 comprises a translucent arced member which allows for visualization of an ALL through the device. By aligning the peripheral boundaries of an ALL on either side of a central portion 102 of the device, a center line of an ALL and associated central axis of a spinal column may be indicated by various components of the present invention, such as indicia 98. In one embodiment, the device further comprises an activator device 74 which activates a marking device. Marking devices of the present invention may include, for example, light or laser emitters, chisels, Bovie® pens, and similar tools.

Figure 7:
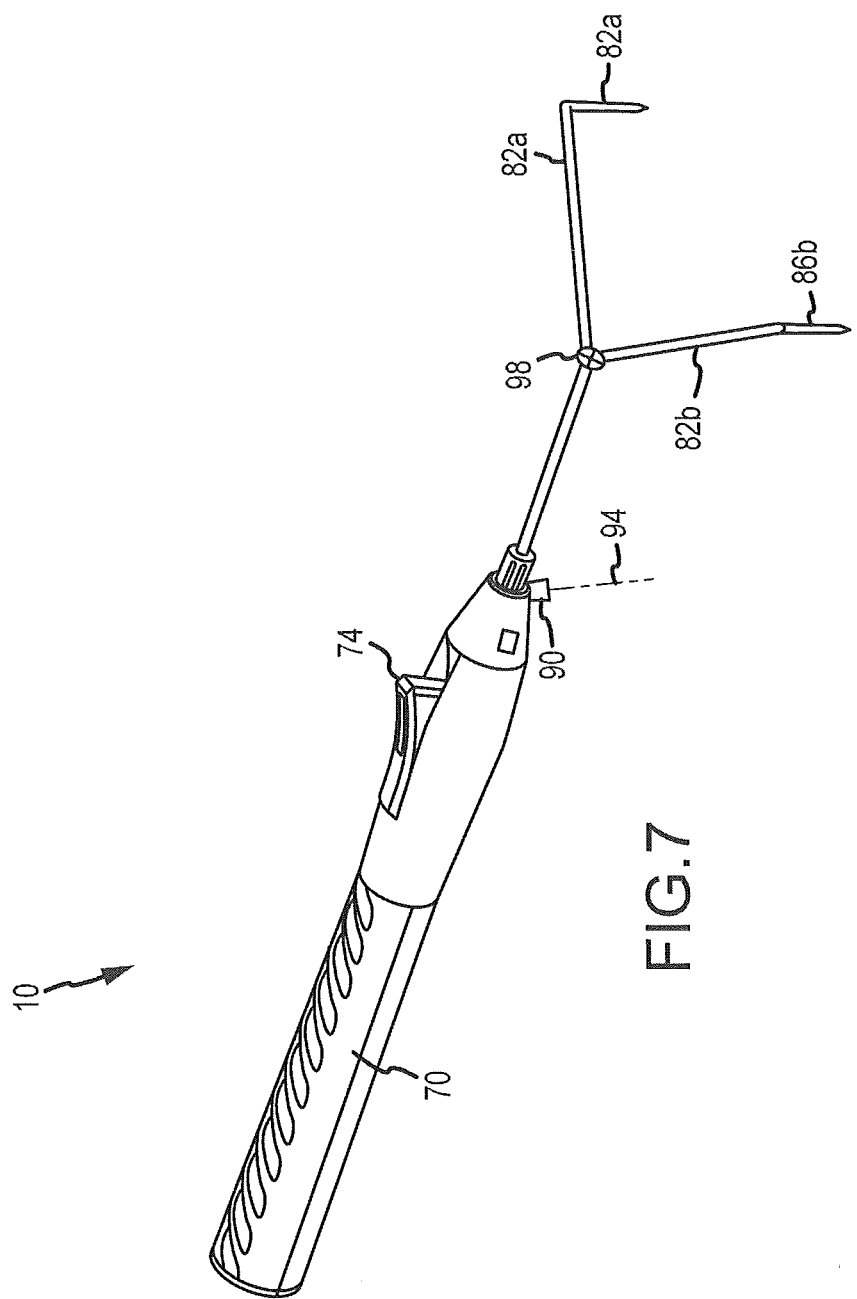
FIG. 7 is a perspective view of yet another device for identification of a center of a spinal column according to one embodiment.

FIGS. 6-7 depict embodiments wherein a handheld portion 70 is provided to allow a user to easily grip the device 10. Extending member 82A, 82B are provided with perpendicular extending member 86A, 86B capable of determining the peripheral boundaries of an ALL. In one embodiment, members 82A, 82B are hinged and controlled by a user such that they may be contracted (e.g. by a push button) without requiring the use of two hands. In one embodiment, the invention further comprises a marking device 90, such a laser emitting device which projects a line or point 94. For example, once the device 10 and members 82A, 82B are appropriately positioned, a trigger member 74 may be activated to project a laser line and/or point. Those of skill in the art will recognize that various handheld portions 70 as shown and described may be used in conjunction with various different ALL measuring/centering devices as described herein. Thus, the present invention is not limited to any specific combination or arrangement of the novel devices shown and described herein.

Accordingly, a method of use of the present invention is provided wherein a disc space centering tool may be employed within a surgical workspace to identify a center or midline of a spinal column. In disc arthroplasty procedures, it is desirable to place a replacement disc as close to the center of a rotational axis of the spine as possible. A tolerance of 3 mm of displacement between the central axis of the spine and the center of an implanted artificial disc is preferred, although tighter tolerance is typically desired. In one embodiment, hinged members 18a, 18b may be expanded to a desired width and generally situated so that hinged members 18a, 18b are positioned on either side of an ALL 14. Concurrently, an indicating member 50 may be rotated upward so that it does not impair movement or visibility of the device 10. Once hinged members 18a, 18b are generally situated on either side of an ALL 14, hinged members 18a, 18b may be contracted to a position where both hinged members 18a, 18b contact the lateral boundaries of the ALL 14.

In one embodiment, a user may determine the existence of contact between aspects of the present invention and an ALL 14 through visual observation and/or tactile sensation. In another embodiment, the presence of this contact may be communicated to a user by various sensing means. For example, touch-sensors or similar devices may be implemented into a distal portion of hinged members 18a, 18b that are capable of determining contact between the present invention and an ALL 14. Upon contact with an ALL 14, touch-sensors of the present invention may provide feedback to a user, such as through visual light indicators or audio indicators, that contact has been made and no further contraction of hinged members 18a, 18b is required.

Once the hinged members 18a, 18b have been brought into contact with an ALL 14 or other object whose center line is to be determined, indicating member 50 may then be useful for identifying, targeting, and/or marking a center line of the object identified by hinged members 18a, 18b as previously described. Those of skill in the art will recognize that that longitudinal position of indicating member 50 will vary as a function of its rotational positional about an axis z, the rotation or tilt of the device 10, and the lengths of the hinged members 18a, 18b and indicating member 50. Accordingly, various spans or distances d between a distal point of hinged members 18a, 18b and indicating member 50 may be achieved. Those of skill in the art will recognize the inherent utility in this feature as different distances d will be desired based on variations in patient size and portion of the spine under consideration.

Once a center line has been identified as previously described, it may be marked by various different methods and devices. In one embodiment, indicating member 50 further comprises means for marking an ALL 14 or object whose center line is to be located. For example, the distal end of an indicating member 50 may comprise an electrode containing device capable of marking a point representative of a spinal center line. Accordingly, once the device 10 is properly positioned, a user may activate the features of such a device to cauterize or mark a point which is to serve as a visual indicator of a center line for the remainder of surgical procedures to be performed. In one embodiment, indicating member 50 may include a through-hole through its center capable of accommodating various devices useful for marking a point, such as a Bovie® pen or similar electrode containing device, chisel, or other marking device. In this embodiment, a center line may be marked or indicated by inserting the appropriate device within indicating member 50 and performing the appropriate function (e.g. activating the electrode pen or tamping down a chisel to provide a mark). A spinal center line or other location may also be marked using various dyes and inks as described herein. Once procedures are completed, various components as described herein may be discarded or properly sanitized for reuse.

According to various embodiments, once a center line has been determined and the appropriate mark or indication made, the device 10 may be removed from the work area. It will be recognized, however, that the device 10 may be left within a surgical workspace and continue to serve as a reference point for a center line. For example, where procedures are to be conducted which do not require the level of access and freedom of movement provided by the removal of the device 10, the device 10 may remain within the workspace as a physical indicator of a center line.

In another embodiment, a center line may be marked by rotating the device 10 and an indicating member 50 in a substantially simultaneous manner. It will be recognized that when an indicating member 50 is in contact with an ALL 14 or other object, rotating the indicating member alone about an axis z will either result in merely applying force to the object 14 or rotation of the indicating member 50 away from the object 14. However, it will also be recognized that where the indicating member 50 and the object 10 itself are rotated generally simultaneously, contact between a distal end of an indicating member 50 and an object 14 may be preserved while the distal end of an indicating member 50 translates along a length of the object 14. In this manner and in conjunction with marking devices and methods as previously described, a center line of an ALL 14 or similar object may be marked by a single point, a plurality of points, or a continuous line.

Figure 8:
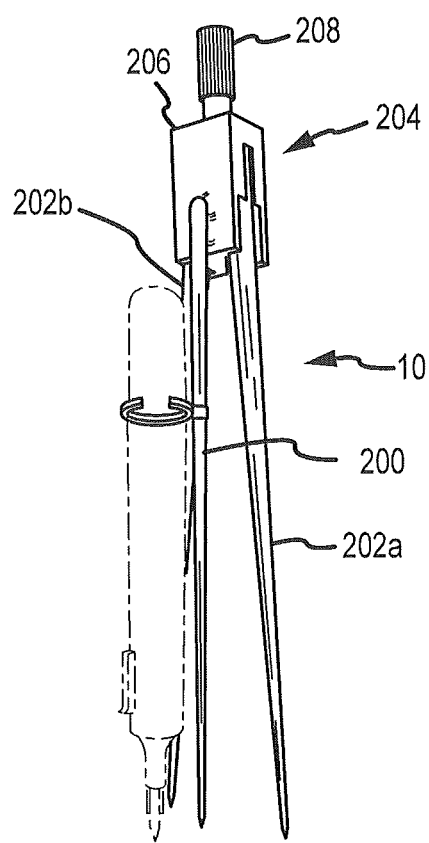
FIG. 8 is a perspective view of a device for identification of a center of a spinal column according to one embodiment.

FIG. 8 depicts another embodiment of the present invention wherein a device 10 is provided with at least one fixedly attached member 200. As shown, an indicating member 200 is provided wherein the indicating member is fixedly attached to a connecting portion 206 and additional members 202a, 202b are hingedly attached and rotatable about a common point. A fixedly attached member 200 may be secured to or in communication with a connection portion 206 via any number of known devices or methods including, but not limited to, press-fitting, tack-welding, bonding, various adhesives, etc. In one embodiment, an adjustment device 208 is provided for adjusting the position of at least hinged members 202A, 202B. Adjustment device 208 is further adapted for use in manipulating or controlling the device 10. In one embodiment, member 208 does not comprise an adjustable portion, but rather is provided so a user may grasp the device 10 at a user-proximal portion. In one embodiment, at least one member of the device 10 comprises telescoping features and/or marking features as shown and described herein.

While various embodiments the present invention have been described in detail, it is apparent that modifications and alterations of those embodiments will occur to those skilled in the art. However, it is to be expressly understood that such modifications and alterations are within the scope and spirit of the present invention, as set forth in the following claims. Further, the invention(s) described herein are capable of other embodiments and of being practiced or of being carried out in various ways. In addition, it is to be understood that the phraseology and terminology used herein is for the purposes of description and should not be regarded as limiting. The use of "including," "comprising," or "adding" and variations thereof herein are meant to encompass the items listed thereafter and equivalents thereof, as well as, additional items.

What is claimed is:

1. A device for identification of a center of a vertebral disc space and corresponding central axis of a spinal column comprising:
   a) a single grasping portion at a user proximal end of said device configured to facilitate a surgeon's manipulation and use of the device, said grasping portion comprising a single handheld extension suited to fit in a surgeon's hand when gripped by a surgeon, thereby facilitating operation of said device without the need to use two hands;
   b) a center-line indicating portion operatively associated with said single grasping portion, said center-line indicating portion having a first component for identifying one border of the patient's anterior longitudinal ligament and a second component for identifying a separate border of the patient's anterior longitudinal ligament, and a third component for marking a point equidistant from each of said borders, said third component having an annular portion sized to accommodate a commercial device selected from the group consisting of a Bovie® pen, a laser emitter and an electrode device, said commercial device received by the annular portion in a manner that facilitates location of a central location between said first and second components and to generate an indication of the location of a particular location,
   c) a connecting portion associated with the grasping portion, said connecting portion hingedly attached to said first component and said second component, said first component and said second component being rotatable about a common point, each of said first and second components having an extended longitudinal axis, with a first end associated with said connecting portion and a second end having a pointed patient-contacting end extending directly in line with said axis; and
   d) an adjustment device for adjusting a position of one of the hingedly attached first component and said second component, wherein said third component is positioned between said first and second components when said first component, second component and third component are adapted to be in contact with a patient's vertical disc space when identifying a center of a vertebral disc space.

2. The device as set forth in claim 1, wherein said device is disposable and said first and second components comprise PEEK.

3. The device as set forth in claim 1, wherein said device further comprises a set screw and a slot in communication with said components to maintain said components in a predetermined position.

4. The device as set forth in claim 1, wherein said first component is comprised of a phosphorescent material.

5. The device as set forth in claim 1, wherein said device comprises disposable components.

6. The device as set forth in claim 1, wherein said first and second components comprise PEEK.

7. The device as set forth in claim 1, wherein said first component and said second component have similar length and dimensions.

8. The device as set forth in claim 1, further comprising a trigger mechanism employed to permit a surgeon to depress a trigger and move the first and second components.

9. The device as set forth in claim 1, wherein said grasping portion includes a button or dial.

10. The device as set forth in claim 1, wherein at least one of said first component and second component comprise a proximity sensor.

11. The device as set forth in claim 1, wherein said grasping portion includes an actuator that activates said commercial device to make a temporary mark at a measured equidistant point.

12. The device as set forth in claim 1, wherein said device comprises a translucent material.

13. The device as set forth in claim 1, wherein said device further comprises a magnifying lens positioned to provide visualization of a surgical work space.

14. The device as set forth in claim 1, wherein said device further comprises a source of illumination.

15. The device as set forth in claim 1, wherein one of said first and second components comprises a telescoping member.

16. The device as set forth in claim 1, wherein said device is configured to operably interfaces with one of a surgical microscope, a computer aided remote surgical operation system and an ultrasonic diagnostic system.

17. The device as set forth in claim 1, further comprising an activator device comprising a laser.

* * * * *